(12) United States Patent
Lechot

(10) Patent No.: US 6,238,398 B1
(45) Date of Patent: May 29, 2001

(54) SURGICAL REAMER

(75) Inventor: André Lechot, Orvin (CH)

(73) Assignee: Precifar S.A., Orvin (CH)

( * ) Notice: Subject to any disclaimer, the term of this patent is extended or adjusted under 35 U.S.C. 154(b) by 0 days.

(21) Appl. No.: 09/332,461

(22) Filed: Jun. 14, 1999

(30) Foreign Application Priority Data

Jun. 17, 1998 (CH) .................................. 1302/98

(51) Int. Cl.⁷ .................................. A61B 17/00
(52) U.S. Cl. .................................. 606/80; 606/79
(58) Field of Search .................................. 606/80, 79

(56) References Cited

U.S. PATENT DOCUMENTS

| 2,746,722 | 5/1956 | Schneider et al. | 606/80 |
| 4,751,922 | 6/1988 | Dipietropolo | 606/80 |
| 5,122,134 | 6/1992 | Borzone et al. | 606/80 |
| 5,690,634 | 11/1997 | Muller et al. | 606/80 |

FOREIGN PATENT DOCUMENTS

| 296 16 633 U | 11/1996 | (DE) . |
| 0 440 317A | 8/1991 | (EP) . |
| 0 648 477A | 4/1995 | (EP) . |

*Primary Examiner*—Gary Jackson
(74) *Attorney, Agent, or Firm*—Bugnion S.A.; John Moetteli

(57) ABSTRACT

Surgical reamer consisting of a cutting head integral with a drive rod for driving it in rotation. The cutting head has, to the rear, auxiliary cutting teeth whose cutting edges are oriented alternately rightward and leftward in such a way as to permit easy withdrawal of the reamer, by the cutting effect of said teeth, in both directions of rotation.

1 Claim, 1 Drawing Sheet

SURGICAL REAMER

BACKGROUND OF THE INVENTION

The subject of the present invention is a surgical reamer consisting of a rod driven in rotation, equipped with a cutting head having, toward the rear, auxiliary cutting teeth permitting easy withdrawal of the reamer.

Reamers are used in surgery to prepare canals in the bones which are intended to receive implants. These reamers generally have a hollow cutting head which is conical, more precisely, frustoconical. This head is often fixed to the end of a flexible or rigid rod formed by at least one helically wound band of steel. The cutting work in the bone wall has the effect of forming bone chips mixed with a spongy mass. Upon withdrawal of the reamer by the surgeon, this mass has a tendency to cause packing, which slows down the reamer, still continuing to turn, by exerting on the latter a high resistance torque. This resistance torque can even lead to fracturing of part of the reamer. In the case of a flexible rod, this resistance torque can soon cause deformation of the flexible rod. The resistance is particularly great when the surgeon removes the reamer by turning it in the direction counter to the prescribed direction.

In order to facilitate withdrawal of the reamer, it has been proposed to form auxiliary cutting teeth on a frustoconical part to the rear of the head of the reamer. Reamers of this type are described in U.S. Pat. No. 5,122,134, the content of which is incorporated by reference. The auxiliary cutting teeth of these reamers are formed along the continuation of the helices of the principal teeth. These auxiliary cutting teeth permit an easy withdrawal movement of the reamer by virtue of the cutting effect of the teeth situated toward the rear of the reamer. Upon withdrawal of the reamer, the auxiliary teeth cut the bone chips. The spongy mass and the bone chips are able to pass, without causing packing along the flutes formed between the auxiliary teeth.

To achieve the desired favorable effect, the reamer must turn in a defined direction during withdrawal. However, it often happens that the surgeon removes the reamer by turning it in the direction counter to the prescribed direction. Therefore, a need exists for a reamer which avoids the hazards of removal, present in the prior art.

SUMMARY OF THE INVENTION

The object of the present invention is to provide the surgeon with a reamer which is easy to withdraw irrespective of the direction of rotation, in such a way that the surgeon does not need to concern himself with the direction of rotation of the reamer.

In the reamer according to the invention, the cutting edges of the auxiliary teeth are oriented alternately leftward and rightward in such a way as to ensure cutting in both directions of rotation.

The number of teeth may be even or not.

BRIEF DESCRIPTION OF THE DRAWING(S)

The attached drawing shows an illustrative embodiment of the reamer according to the invention.

DETAILED DESCRIPTION OF THE PREFERRED EMBODIMENT(S)

Figure 2:
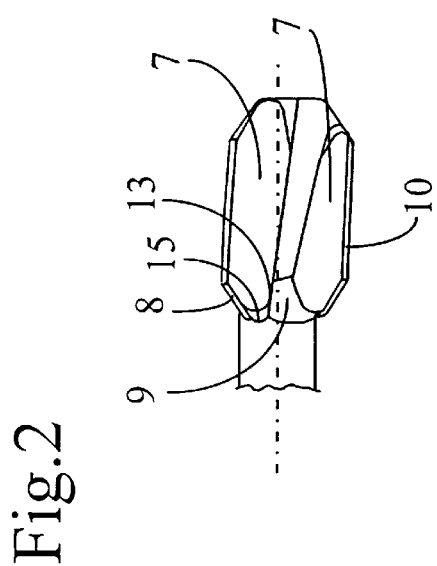
FIG. 2 shows the rear of the cutting head in a second angular position offset by one tooth relative to the first position.
Figure 1:
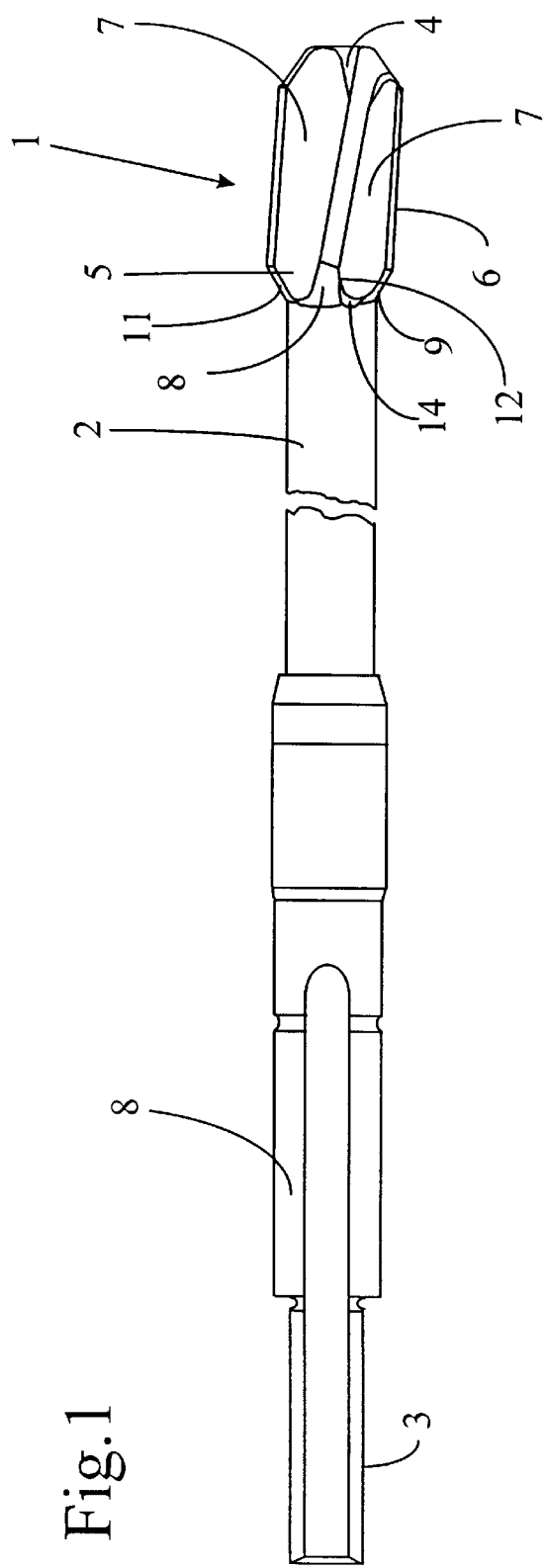
FIG. 1 shows the reamer in a first angular position of its cutting head.

The reamer shown in FIG. 1 comprises a cutting head 1 formed at the end of a rigid rod 2 which is itself welded to a shank 3 intended to be connected to a drive machine. The cutting head 1 has two frustoconical ends 4 and 5 which are connected via a cylindrical central part 6. The head 1 is traversed fully by four helicoidal flutes 7. The four teeth of the front toothing 4 or principal toothing are formed in such a way as to cut for a rightward rotation. The rear frustoconical part 5 is equipped with a toothing which is formed in such a way that the angles of attack and of relief of the four teeth are alternately to one side and the other of the teeth in such a way that this rear part cuts both in one direction of rotation and in the other. In the figures, it will be seen that the teeth 8 and 10 are formed in such a way as to cut during rightward rotation, whereas the adjacent teeth 9 and 11 are formed in such a way as to cut during leftward rotation. The cutting edges are thus, for example, situated respectively on the sides 12 and 13 of the teeth 8 and 9, likewise the reliefs 14 and 15.

The reamer can be withdrawn by rightward rotation, by leftward rotation, or by alternate rightward/leftward rotation.

The rigid rod 2 could of course be replaced by a flexible rod formed preferably by helical winding, in opposite directions, of two bands of steel.

Although illustrative embodiments of the invention have been shown and described, a wide range of modification, change and substitution is contemplated in the foregoing disclosure and in some instances, some features of the present invention may be employed without a corresponding use of the other features. Accordingly, it is appropriate that the appended claims be construed broadly and in a manner consistent with the scope of the invention.

What is claimed is:

1. A surgical reamer consisting of a rod (2) driven in rotation, equipped with a cutting head (1) having cutting teeth (4) and, toward the rear, auxiliary cutting teeth (5) permitting easy withdrawal of the reamer, wherein the cutting edges of the auxiliary teeth (5) are formed from the same flutes as the cutting teeth (4) and are oriented both leftward and rightward in such a way as to ensure cutting in both directions of rotation.

* * * * *